(12) United States Patent
Gabbay (10) Patent No.: US 6,368,348 B1
(45) Date of Patent: Apr. 9, 2002

(54) ANNULOPLASTY PROSTHESIS FOR SUPPORTING AN ANNULUS OF A HEART VALVE

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 0 days.

(21) Appl. No.: 09/570,891

(22) Filed: May 15, 2000

(51) Int. Cl.[7] .................................................. A61F 2/24
(52) U.S. Cl. ..................................... 623/2.36; 623/2.17
(58) Field of Search ............................. 623/2.36, 2.37, 623/2.38, 2.39, 2.4, 2.41, 2.42

(56) References Cited

U.S. PATENT DOCUMENTS

| | | | |
|---|---|---|---|
| 4,042,979 A | 8/1977 | Angell | 3/1.5 |
| 4,350,492 A | 9/1982 | Wright et al. | 8/94.11 |
| 4,491,986 A * | 1/1985 | Gabby | 623/2.36 |
| 5,104,407 A | 4/1992 | Lam et al. | 623/2 |
| 5,584,879 A | 12/1996 | Reimold et al. | 623/2 |
| 5,716,397 A | 2/1998 | Myers | 623/2 |
| 5,824,066 A | 10/1998 | Gross | 623/2 |
| 6,092,529 A * | 7/2000 | Cox | 128/898 |
| 6,102,945 A * | 8/2000 | Campbell | 623/2.37 |
| 6,174,332 B1 * | 1/2001 | Loch et al. | 623/2.37 |
| 6,183,512 B1 * | 2/2001 | Howanec, Jr. et al. | 623/2.36 |
| 6,187,040 B1 * | 2/2001 | Wright | 623/2.36 |
| 6,217,610 B1 * | 4/2001 | Carpentier et al. | 623/2.37 |

OTHER PUBLICATIONS

Heart Valves, The Duran Flexible Annuloplasty Ring. Product Information for The Duran Flexible Annuloplasty Ring, by Medtronic, Inc.; 4 pages; Http://www.medtronic.com/cardiac/heartvalves/duran ring/. (Bearing copyright date of 2000).
Carpentier, Alain. Mitral Valve Reconstructive Surgery. Paris, France. Pp. 405–414. (date unknown).

* cited by examiner

Primary Examiner—David H. Willse
Assistant Examiner—Suzette J. Jackson
(74) Attorney, Agent, or Firm—Amin & Turocy, LLP

(57) ABSTRACT

An annuloplasty prosthesis for supporting an annulus of a heart valve includes a substrate material over which a covering of a biocompatible and biological tissue material is applied. The substrate may be formed of a generally rigid material (e.g., a plastic or metal) in which the substrate has a predetermined shape corresponding to an annulus of the heart valve. Alternatively, the substrate may be formed of flexible material (e.g., a soft cloth or natural tissue), which may be adjusted at implantation to accommodate the size and configuration of annulus.

38 Claims, 5 Drawing Sheets

Fig.15C

ANNULOPLASTY PROSTHESIS FOR SUPPORTING AN ANNULUS OF A HEART VALVE

TECHNICAL FIELD

The present invention relates to an implantable support and, more particularly, to an annuloplasty prosthesis for supporting an annulus of a heart valve.

BACKGROUND

A heart valve, such as a mitral or tricuspid valve, may become defective or damaged, such as resulting from congenital malformation, disease or aging. When the valve becomes defective or damaged, the leaflets may not function properly. One common problem associated with a degenerating heart valve is an enlargement of the valve annulus (e.g., dilation). The annulus, for example, may enlarge or dilate to a point where the attached leaflets are unable to fully close, which may lead to regurgitation. As a result, surgical correction, either by valve repair procedures or by valve replacement, may be required.

Surgical reconstruction or repair procedures may include plication, chordal shortening, or chordal replacement. Another common repair procedure relates to remodeling of the valve annulus (e.g., annuloplasty), which may be accomplished by implantation of a prosthetic ring to help stabilize the annulus and to correct or prevent valvular insufficiency which may result from defect or dysfunction of the valve annulus. By properly sizing and implanting the annuloplasty ring, the valve annulus can be substantially restored to its normal, undilated, circumference.

Typically, annuloplasty rings are in the form of a rigid or flexible plastic material covered with a biocompatible cloth-like material, such as a Dacron® polymer fabric. The cloth-like covering, however, provides a site at which blood may clot. In addition, the covering may cause blood elements to coagulate and, in turn, cause thromboembolic events. As a result, a recipient of a conventional annuloplasty ring may require re-operation, thereby presenting undesirable risks to the patient.

SUMMARY

The present invention provides an annuloplasty prosthesis for supporting an annulus of a heart valve. The prosthesis includes a substrate material over which a covering of a biocompatible biological tissue material, such as animal pericardium, is applied. The substrate may be formed of a generally rigid material (e.g., a plastic or metal) in which the substrate has a predetermined shape corresponding to an annulus of the heart valve. Alternatively, the substrate may be formed of flexible material (e.g., a soft cloth or natural tissue), which may be adjusted at implantation to accommodate the size and configuration of an annulus.

An aspect of the present invention provides an annuloplasty prosthesis for supporting an annulus of a heart valve. The annuloplasty prosthesis includes a tubular sheath of an animal tissue material having a lumen within the sheath. A length of a substrate is disposed within the lumen to facilitate implantation of the sheath at an annulus of a heart valve.

Another aspect of the present invention provides an annuloplasty prosthesis for supporting an annulus of a heart valve. The annuloplasty prosthesis includes a generally C-shaped substrate of a substantially resilient material having spaced apart ends. A sheath of an animal tissue material covers the C-shaped substrate and an implantation flange extends outwardly from a sidewall portion of the sheath.

Yet another aspect of the present invention provides an annuloplasty prosthesis for supporting an annulus of a heart valve. The annuloplasty prosthesis includes a substrate, which may be substantially flexible or resilient. A sheath of biocompatible animal tissue (e.g., animal pericardium) covers the substrate. A bridge of a flexible material extends between the ends of the substrate so as to form a generally D-shaped prosthesis. To provide additional stiffness to the structure a generally rigid or resilient rod may be disposed within the bridge of flexible material.

To the accomplishment of the foregoing and related ends, the invention, then, comprises the features hereinafter fully described and particularly pointed out in the claims. The following description and the annexed drawings set forth in detail certain illustrative aspects of the invention. These aspects are indicative, however, of but a few of the various ways in which the principles of the invention may be employed. Other objects, advantages and novel features of the invention will become apparent from the following detailed description of the invention when considered in conjunction with the drawings.

DESCRIPTION

Figures 1, 1A:
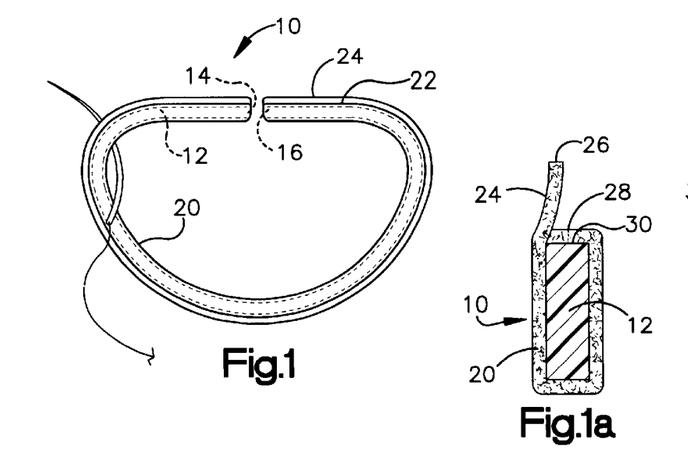
FIG. 1 is a top view of a prosthesis in accordance with the present invention.
FIG. 1A is a side sectional view of the prosthesis of FIG. 1 illustrating an example of an implantation flange.

FIG. 1 illustrates an example of an annuloplasty prosthesis 10 for supporting an annulus of a heart valve in accordance with an aspect of the present invention. The prosthesis 10 includes a generally C-shaped substrate 12 having ends 14 and 16 that are spaced apart from each other. In this example, the substrate 12 may be formed of a generally resilient material or a generally rigid material having an elastic property so as to return to its original shape when deflected from its original (or rest) condition. The substrate 12, for example, may be a plastic-like material (e.g., a polymer, a resin, etc.) or a metal (e.g., stainless steel), such as in the form of a wire. It will be understood and appreciated that other types of generally rigid, elastic, and/or resilient materials also may be used in accordance with the present invention.

An outer sheath 20 of a biological tissue material 20 completely covers the substrate 12. For example, an elongated sheet (or strip) of an appropriate biocompatible animal tissue material may be wrapped around the substrate 12 to form a generally tubular structure around the substrate. The substrate 12, thus, is disposed within a lumen 22 extending longitudinally through the tubular outer sheath 20.

The biological tissue, for example, is smooth animal pericardium (e.g., equine, bovine, porcine, etc.) that has been tanned or fixed in a suitable tanning environment. The pericardium, for example, is cross-linked with glutaraldehyde and undergoes a detoxification process with heparin bonding, such as one of the NO-REACT® natural tissue products that are commercially available from Shelhigh, Inc. of Millburn, N.J. The NO-REACT® natural tissue products exhibit improved biocompatibility and mitigate calcification and thrombus formation.

The prosthesis 10 also includes an implantation flange (or sewing ring) 24 extending from an outer peripheral edge of the prosthesis. The implantation flange 24 facilitates implantation of the prosthesis 10. With reference to FIG. 1A, the outer sheath 20 may have one edge 26 that extends outwardly from the substrate to define the implantation flange 24. The other edge 28 covers an outer peripheral edge 30 of the substrate 12 and is connected to a proximal part of the flange 24, such as by sutures (not shown).

Figure 1B:
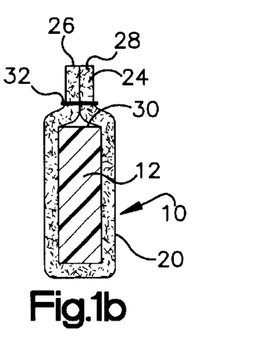
FIG. 1B is a side sectional view of the prosthesis of FIG. 1 illustrating another example of an implantation flange.

Alternatively, as shown in FIG. 1B, the implantation flange 24 may be formed of a double layer of the animal tissue material extending from an outer peripheral edge of the prosthesis 10. In this example, both side edges 26 and 28 extend outwardly from the outer edge 30 of the substrate 12 to define the implantation flange 24. One or more sutures 32 connect the laterally extending side edge layers 26 and 28 of the implantation flange 24 so that the implantation flange maintains its outwardly extending position. The sutures 32 also may secure the sheath relative to the substrate 12.

While the examples of FIGS. 1A and 1B illustrate the implantation flange 24 as having one and two layers, respectively, it is to be understood and appreciated that the implantation flange may, in accordance with the present invention, be formed of any number of layers of flexible material, such as animal pericardium. Alternatively, another flexible biocompatible material, such as collagen, may be attached at the outer periphery 22 of the substrate to form an implantation flange.

Figures 2, 3:
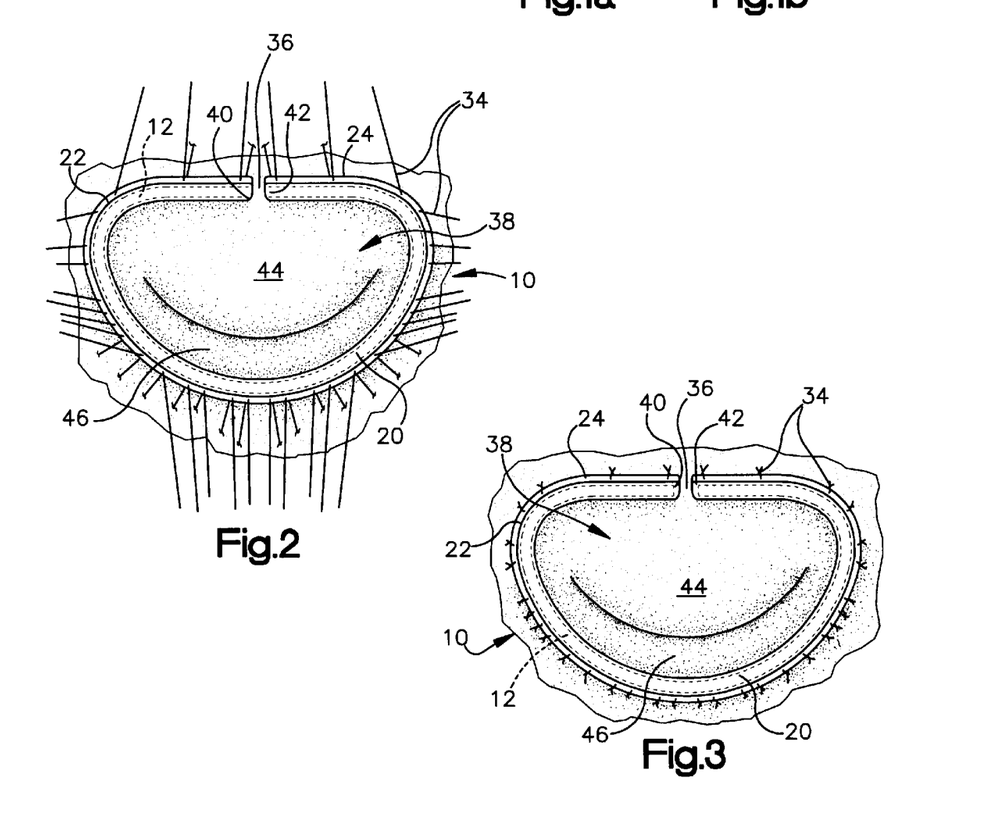
FIG. 2 is a top view of the prosthesis of FIG. 1 showing an intermediate step in the implantation process in accordance with the present invention.
FIG. 3 is a top view of the prosthesis of FIG. 1 illustrating the prosthesis implanted at an annulus of a valve in accordance with the present invention.

FIG. 2 illustrates an implantation step during which sutures 34 are employed to mount the prosthesis 10 to a distended annulus 36 of mitral valve 38 in accordance with an aspect of the present invention. In particular, opposed ends 40 and 42 of the generally C-shaped prosthesis (adjacent ends 14 and 16 of the substrate 12) are positioned along annulus adjacent the anterior leaflet and the other part of the prosthesis is positioned along the posterior leaflet. The sutures 34 are applied to the implantation flange 24 encircling the prosthesis 10 for securing the prosthesis relative to the annulus at a desired position.

The annuloplasty prosthesis 10 is urged into contact with the annulus 36 and the sutures 34 are then tied off so that the implanted prosthesis engages and is attached at the annulus 36, as shown in FIG. 3. The prosthesis 10 advantageously operates to retain the annulus 36 in its normal physiologic shape. The implanted prosthesis 10 having a semi-rigid or elastic substrate also enables the annulus to exhibit proper dynamics during systole and diastole, as the C-shaped portion of the prosthesis permits movement of the annulus at diastole and supports the annulus to improve coaptation at systole. As a result, a valve having a distended annulus that is equipped with an annuloplasty ring, in accordance with the present invention, provides improved hemodynamics. In addition, the biological tissue covering, such as a NO-REACT® tissue covering, provides an anti-calcification effect as well as mitigates formation of blood clots.

Figure 4:
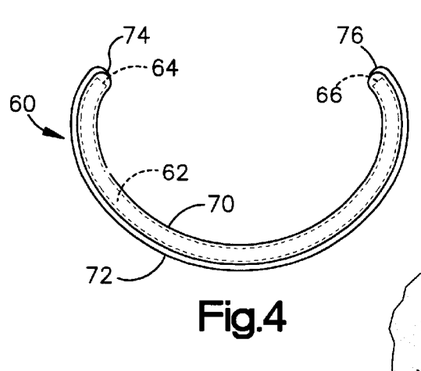
FIG. 4 is a top view of a second example of a prosthesis in accordance with the present invention.
Figure 5:
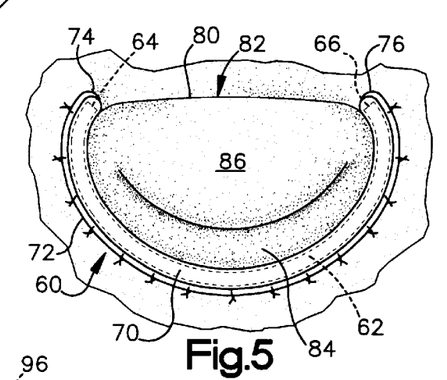
FIG. 5 is a top view of the prosthesis of FIG. 4, illustrating the prosthesis implanted at an annulus of a valve in accordance with the present invention

FIGS. 4 and 5 illustrate an example of an annuloplasty prosthesis 60 in accordance with another aspect of the present invention. The prosthesis 60 includes a generally C-shaped substrate 62 having opposed ends 64 and 66 that are spaced apart from each other. The opposed ends 64 and 66 are spaced apart from each other a greater distance than the example shown and described with respect to FIGS. 1–3. The substrate 62 may formed of a resilient, flexible or generally rigid material, such as described herein.

An outer sheath 70 of a biological tissue material completely covers the substrate 62 so that the substrate is not exposed. The biological tissue material may be an animal tissue material (e.g., biocompatible animal pericardium), such as described above with respect to FIGS. 1–3. The prosthesis 60 also includes an implantation flange (or sewing ring) 72 extending from an outer peripheral edge of the prosthesis 60. The implantation flange 72 is formed of a flexible material and, as described with respect to FIGS. 1A and 1B, may be formed from part of the biological tissue material covering the substrate 62. The biological tissue covering also covers the ends 64 and 66 of the substrate 62 to define opposed ends 74 and 76 of the prosthesis 60.

FIG. 5 illustrates the prosthesis 60 of FIG. 4 implanted at an annulus 80 of a mitral (or bicuspid) valve 82, although the prosthesis may be used to support other types of heart valves (e.g., a tricuspid valve). The prosthesis 60 is dimensioned and configured to have an annular length and configuration that, when implanted, approximates a posterior extent of the valve annulus 80 relative to the leaflet 84. As a result, when the prosthesis 60 is implanted, the prosthesis 60 provides little direct support the valve 82 from an anterior position relative to the valve. The portion of the valve annulus 80 anterior the leaflet 86 remains substantially free to move, as no prosthesis is attached at that annulus portion.

Figure 6:
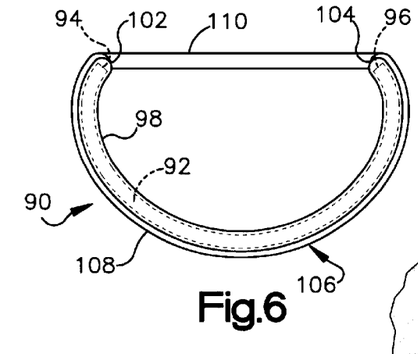
FIG. 6 is a top view of third example of a prosthesis in accordance with the present invention.
Figure 7:
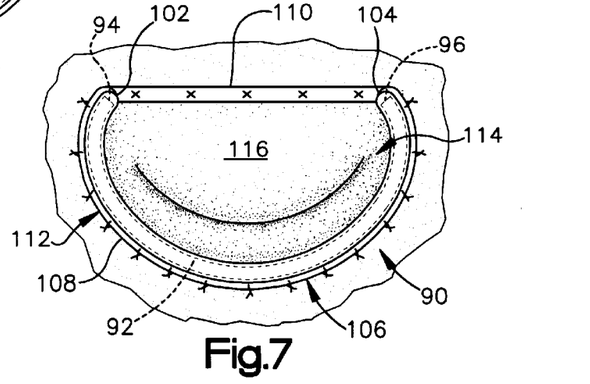
FIG. 7 is a top view of the prosthesis of FIG. 6, illustrating the prosthesis implanted at an annulus of a valve in accordance with the present invention.

FIGS. 6 and 7 illustrate an example of annuloplasty ring prosthesis 90 in accordance with another aspect of the present invention. The basic configuration is substantially identical to that shown and described with respect to FIGS. 4 and 5. Briefly stated, the prosthesis 90 includes an C-shaped ring substrate 92 having spaced apart opposed ends 94 and 96. An outer sheath 98 of a biocompatible biological tissue, such as animal pericardium, completely covers the C-shaped ring 92. The outer sheath 98 covers the ends 94 and 96 of the substrate 92 to define opposed ends 102 and 104, respectively, of a C-shaped portion 106 of the prosthesis 90. An implantation flange (or sewing ring) 108 of a flexible material extends from an outer peripheral edge of the outer sheath. The implantation flange 108 may be formed from an outwardly extending part of the outer sheath 98 or a separate elongated strip of a flexible material connected to the outermost periphery of the prosthesis 90 along the C-shaped portion 106.

In accordance with an aspect of the present invention, the prosthesis 90 also includes a length 110 of a flexible material extending between the end portions 102 and 104 of the C-shaped portion 106 of the prosthesis, so as to form a generally D-shaped ring-like prosthesis structure, as shown in FIGS. 6 and 7. In other words, the length 110 of flexible material forms a bridge (hereinafter the "bridge 110") interconnecting the ends 102 and 104 of C-shaped portion 106. The bridge 110 may be formed of a biocompatible animal tissue material. For example, the length 110 of flexible material may be animal (porcine, bovine, equine, etc.) pericardium that has been cross-linked with an appropriated glutaraldehyde solution and subjected to an anti-calcification process, such as a length of a NO-REACT® tissue product. Those skilled in the art will appreciate and understand, however, that any other flexible material (e.g., polymer, collagen, cloth-like material, etc.) also could be used to form the bridge 110 in accordance with the present invention.

The bridge 110 also may be formed as an integral part of the outer sheath 98. A length of the biocompatible biological material may be employed that is sufficient to cover the C-shaped substrate 92 as well as connect between the opposed ends 94 and 96 thereof so as to form a complete ring. For example, a length of the outer sheath 98 is extended around the C-shaped substrate to form a generally D-shaped cylindrical ring, with the ends of the sheath overlapping or at least abutting. The edges are folded around the C-shaped ring and attached to each other, such as by sutures. The implantation flange 108 also may be formed from the outer sheath 98, such as shown and described with respect to FIGS. 1A and 1B, extending outwardly from the C-shaped portion. The portion of material that may be used to form an implantation flange at the bridge may be removed or simply rolled to form the elongated bridge extending between the ends 102 and 104.

The bridge 110 provides a flexible mechanism to facilitate implantation of the annuloplasty prosthesis anterior to the heart valve 114, as shown in FIG. 7. In particular, the implantation flange 108 in conjunction with the bridge 110 of flexible material help facilitate implantation of the prosthesis and ensure that the entire prosthesis 90 may be secured relative to an annulus 112 of a heart valve 114. The bridge 110, which may be more flexible than the C-shaped part of the prosthesis 90, permits a greater amount of annulus movement anterior to the valve 114, such as at diastole, than at the posterior part of the annulus affixed to the C-shaped part 106 of the prosthesis. If a surgeon desires a greater amount of movement at the anterior part of the annulus (e.g., adjacent the anterior leaflet 116) or simply not desire the bridge 110, the bridge simply may be removed from the prosthesis 90, such as by cutting it prior to implantation.

Figures 8, 9:
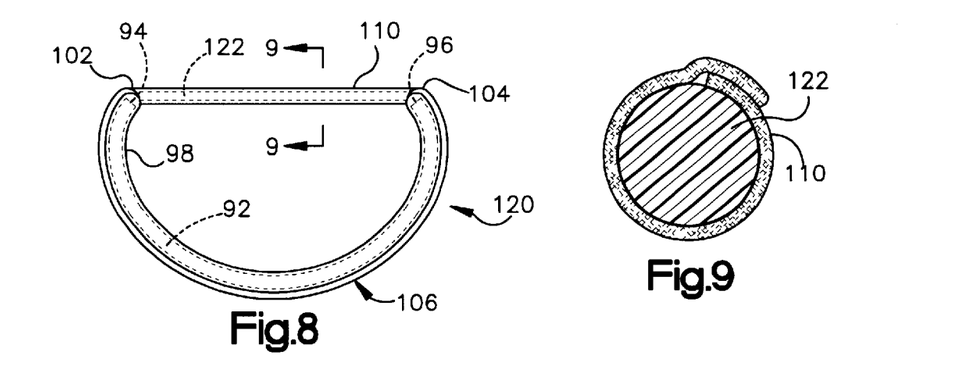
FIG. 8 is a top view of a fourth example of a prosthesis in accordance with the present invention.
FIG. 9 is a dross-sectional view of a bridge portion of the prosthesis of FIG. 8 in accordance with the present invention.

FIGS. 8 and 9 illustrate an annuloplasty ring prosthesis 120 in accordance with another aspect of the present invention, in which identical reference numbers refer to parts previously identified with respect to FIGS. 6 and 7. The prosthesis is substantially similar to that shown and described with respect to FIGS. 6 and 7 and, therefore, a detailed description for this structure has been omitted for sake of brevity.

Referring to FIGS. 8 and 9, an elongated stiffening element 122 is disposed within the bridge 110. The stiffening element 122, for example, is in the form of rod or wire, such as a suitable biological material, plastic, or metal. The length of the stiffening element may approximate a linear distance between the ends 102 and 104 of the C-shaped portion 106. Sutures also may attach the stiffening element 122 directly to the end portions 102 and 104. Alternatively, the stiffening element 122 may have a length that is less than the distance between the ends 102 and 104, being disposed within and supported by the flexible outer layer of biocompatible material (e.g., the bridge 110) that covers the stiffening element. The stiffening element 110 is selected to add a desired amount of support anterior of the annulus when implanted and, in turn, mitigate distortion of the anterior leaflet. Those skilled in the art will appreciate that a more rigid the stiffening element provides less valvular distortion. As in the example of FIGS. 6 and 7, the bridge 110 and the stiffening element 122 may be removed from the prosthesis by simply cutting the structure from the prosthesis, resulting in a structure similar to that of FIGS. 4 and 5.

FIG. 9 illustrates a cross-sectional view of the bridge 110, showing the stiffening element 122 covered in a biocompatible animal tissue outer layer, which may be an integral part of the outer sheath. While the stiffening element 122 is illustrated as a plastic-like material, it is to be understood and appreciated that other materials, such as metal, fabric, etc., also may be utilized. All such materials are contemplated as being within the scope of the present invention.

Figure 10A:
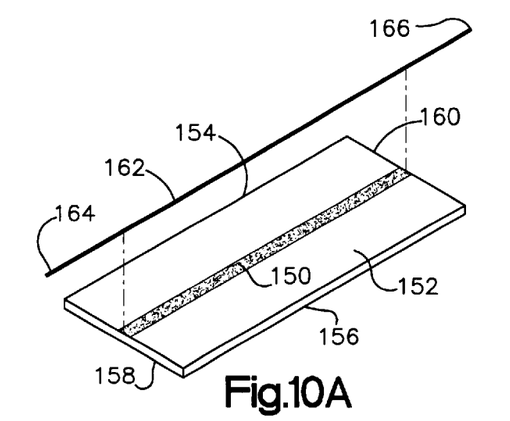
FIG. 10A is a partial exploded view of materials that may be used to form a prosthesis in accordance with the present invention.

FIG. 10A is an exploded view of materials that may be employed to manufacture a flexible annuloplasty prosthesis in accordance with another aspect of the present invention. A substantially flexible substrate material 150 is disposed longitudinally along a sheet 152 of biocompatible animal tissue material. The substrate 150 may be a soft core of silicone rubber impregnated with a radiopaque material (e.g., barium sulfate). The sheet 152, for example, is a NO-REACT natural tissue product (as described hereinabove), although other types of biocompatible animal tissue also may be used. The sheet 152 has side edges 154 and 156 extending between spaced apart ends 158 and 160. A chord 162, such as a soft string or suture, also is provided for forming a purse string mechanism, as described below. The chord 162 is placed over the substrate 150 extending longitudinally along the sheet 152. Opposed ends 164 and 166 of the chord 162 extend beyond the ends 158 and 160 of the sheet 152.

Alternatively, the chord 162 may be impregnated with an radiopaque material and the soft-core material omitted.

Another alternative is to form the substrate 150 from one or more chords disposed within a lumen extending through the rolled structure (FIG. 10B), such as a barium impregnated string or a metal wire material.

Figure 10B:
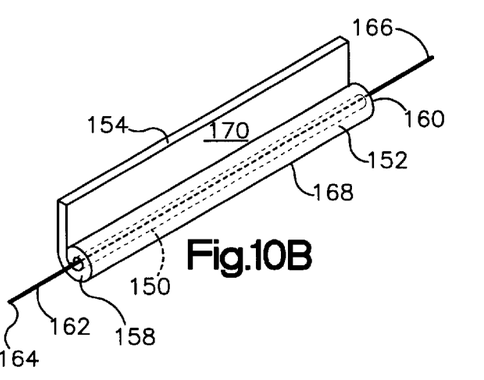
FIG. 10B is an isometric view of the assembled structure of FIG. 10A that may be employed as a prosthesis in accordance with the present invention.

With reference to FIG. 10B, the sheet 152 of biological material is rolled between its side edges 156 and 156 around the chord 162 and substrate 150 to form a generally tubular structure. The sheet 152 forms an outer sheath 168 that completely encloses (or covers) the substrate 150 and a length of the chord 152 coextensive with the length of the sheet between ends 158 and 160. Instead of rolling the sheet 152 completely into a circular cylindrical tube, a portion of the sheet adjacent its side edge 154 may extend tangentially from the tubular part of the structure to form an implantation flange 170. The implantation flange 170 may be configured to have a desired length based on the width of the sheet 152 and the amount that the sheet is rolled.

Figure 11:
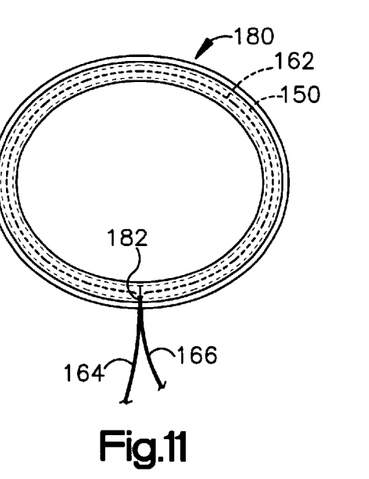
FIG. 11 is a top view of a fifth example of a prosthesis formed from the structure of FIG. 10B in accordance with the present invention.

With reference to FIG. 11, an annuloplasty ring prosthesis 180 may, in accordance with an aspect of the present invention, be formed from the elongated, rolled structure shown of FIG. 10B. For example the ends 158 and 160 of the rolled structure may be urged into abutment and affixed relative to each other by sutures 182 to form the annular prosthesis 180. The chord 162 may be employed to restrict the circumference of the ring. For example, a length of the chord may be pulled from the interior of the outer sheath 168, such as by pulling the ends 164 and 166 of the chord 162 relative to the prosthesis 180, to reduce the circumference of the prosthesis. The ends 164 and 166 of the chord 162 may then be tied relative to prosthesis 180 to fix its circumference. Advantageously, the flexible substrate 150 and chord 162 permit mobility of the annulus when the prosthesis is implanted. A more rigid substrate, of course, also may used if less mobility is desired.

Figure 12A:
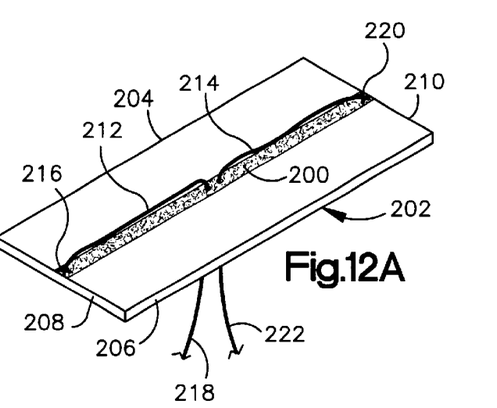
FIG. 12A is a partially assembled view of materials that may be used to form a prosthesis having a purse string in accordance with the present invention.
Figure 12B:
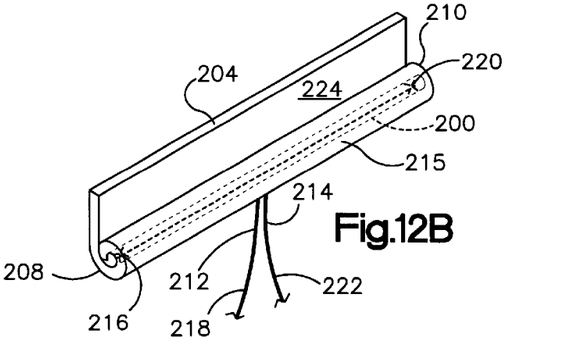
FIG. 12B is an isometric view of an assembled structure of FIG. 12A that may be employed as a prosthesis in accordance with the present invention.

FIGS. 12A and 12B illustrate steps that may be employed to form an annuloplasty prosthesis in accordance with another aspect of the present invention. The materials utilized are similar to those set forth with respect to FIGS. 10A and 10B. Briefly stated, a flexible substrate material 200, such as, for example, a soft core of silicone rubber impregnated with a radiopaque material (e.g., barium sulfate), is disposed longitudinally along a sheet 202 of biocompatible animal tissue material, such as described above. The sheet 202 has side edges 204 and 206 extending between spaced apart ends 208 and 210.

Two lengths of chord 212 and 214, such as soft strings or sutures, are employed to form a purse string mechanism. Each chord 212 and 214 has ends 216, 218 and 220, 222. Ends 216 are 220 are affixed (e.g., by sutures) to corresponding ends 208 and 210 of the sheet 202. A length of the chords are disposed along the substrate to a central part of the sheet and extend through sheet 202 so that ends 218 and 222 extend from a side of the sheet opposite to which chords and substrate 200 are disposed, generally intermediate ends 208 and 210.

FIG. 12B illustrates a structure that may be employed as an annuloplasty prosthesis in accordance with an aspect of the present invention. The sheet 202 is rolled between its side edges 204 and 206 around the substrate 200 and the internal lengths of the chords 212 and 214 to form a generally tubular outer sheath 215 structure. A portion of the sheet 202 adjacent its side edge 204 may extend tangentially from the tubular part of the structure to form an implantation flange 224. The implantation flange 224 may be configured to have a desired length based on the width of the sheet 202 and the amount that the sheet is rolled. The ends 218 and 222 of the chords 212 and 214, respectively, are exteriorized relative to the resulting tubular structure. Each chord 218, 220 may be employed to restrict or adjust a corresponding circumferential arc of a part of the prosthesis.

Figure 13:
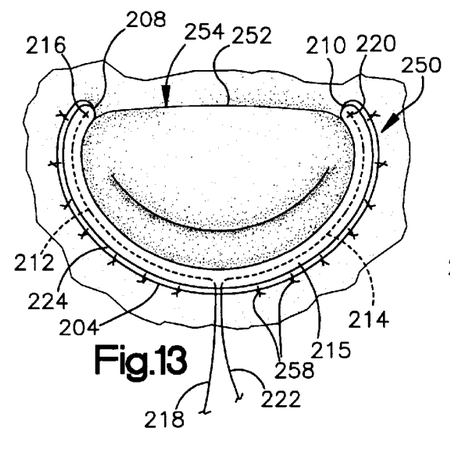
FIG. 13 is a top view of a sixth example of an implanted prosthesis formed from the structure of FIG. 12B in accordance with the present invention.

FIG. 13 illustrates an implanted annuloplasty prosthesis 250, in accordance with an aspect of the present invention, corresponding to the rolled structure of FIG. 12B. Accordingly, like numbers are used to indicate parts previously identified with respect to FIG. 12B. The prosthesis 250 is illustrated as mounted at an annulus 252 of mitral heart valve 254, although the prosthesis may be used to support other heart valves. The annuloplasty prosthesis 250 is bent into a generally C-shaped prosthesis by urging ends 208 and 210 toward each other. Sutures 258 are used to connect the implantation flange 224 along part of the annulus 252 of the valve 254. A length of the chords 212 and 214 are exteriorized relative to the outer sheath 215. The chords 212 and 214 may pulled to a selected length to adjust the annular (or circumferential) length of the prosthesis 250. The chords 212 and 214 may then be tied off so as to inhibit circumferential expansion of the prosthesis 250, while still permitting mobility of the annulus.

Figure 14:
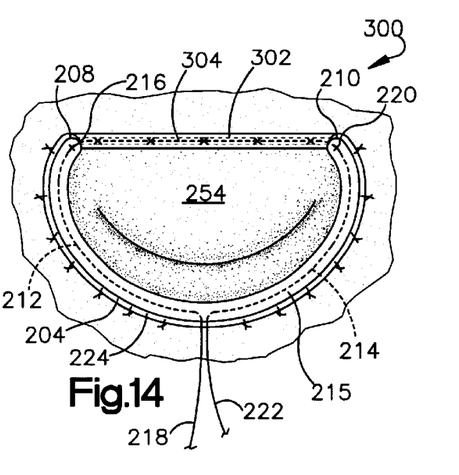
FIG. 14 is a top view of a seventh example of an implanted prosthesis formed from the structure of FIG. 12B in accordance with the present invention.

FIG. 14 illustrates another aspect of an annuloplasty prosthesis 300 in accordance with the present invention. The prosthesis 300 is substantially identical to the prosthesis shown and described with respect to FIG. 13. Identical reference numbers indicates corresponding parts previously identified with respect FIG. 13 and a description of such components has been omitted for sake of brevity.

In accordance with an aspect of the present invention, the prosthesis 300 includes a bridge 302 of a flexible material connected between opposed ends 208 and 210 of the structure of FIG. 12B so as to form a generally D-shaped ring structure. As mentioned above, the bridge 302 may be formed of the same biocompatible animal tissue material as forms the outer sheath. In order to provide additional support at the anterior portion of the valve, a stiffening element 304, such as a wire, rod, or tube, may be disposed within a lumen extending the length of the bridge 302.

As mentioned above, the chords (e.g., sutures) 212 and 214 may be rolled with the soft-core substrate 200, with an end 216 and 220 of each chord connected near a corresponding end 208, 210 of the rolled structure. The other end 218, 222 of each chord is exteriorized through the outer sheath 215 near a midpoint of the rolled structure (see FIG. 12B). Configuring the chords 212 and 214 in this manner provides a purse- or drawstring operation, in which the chords may be employed to restrict and/or adjust the circumference of the prosthesis 300. In particular, when a sufficiently rigid stiffening element 304 is disposed within the bridge 302, the distance between the ends 208 and 210 of the C-shaped part of the structure remains fixed. Accordingly, pulling the chords relative to the prosthesis (pulling a length of each suture from the interior lumen of the C-shaped portion) results in reducing the annular length of the C-shaped portion of the prosthesis 300.

Figure 15A:
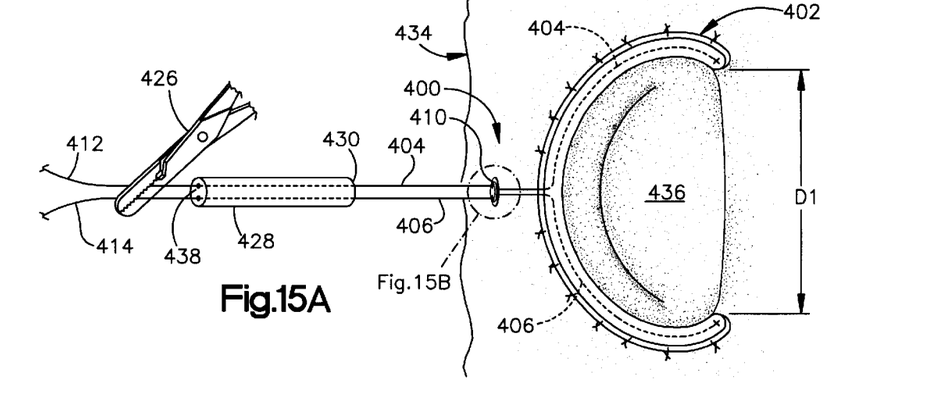
FIG. 15A is a top view of a prosthesis having purse strings, in accordance with the present invention, illustrating a system for adjusting the size of the implanted prosthesis.
Figure 15B:
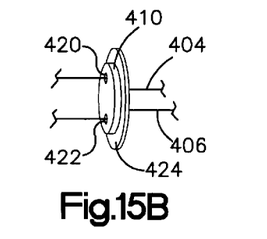
FIG. 15B is an enlarged view of a retaining clip from the system of FIG. 15A in accordance with the present invention.
Figure 15C:
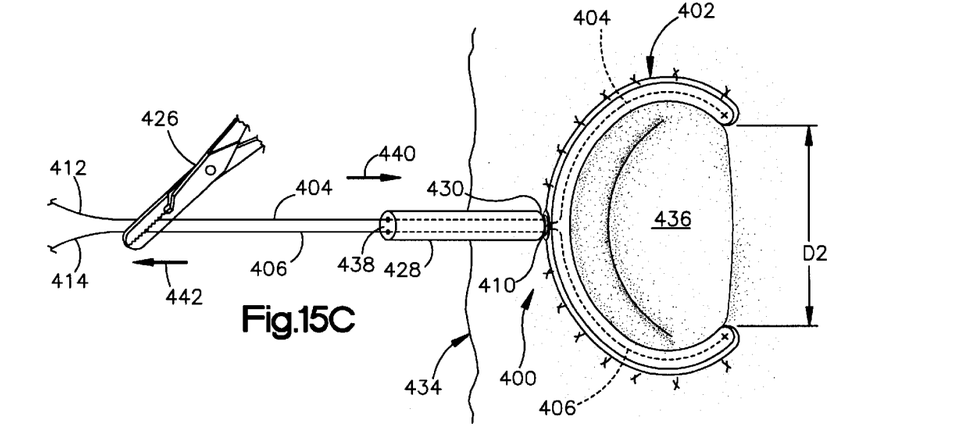
FIG. 15C is another view of the implanted prosthesis of FIG. 15A, illustrating the system in an adjusted condition.

FIGS. 15A, 15B, and 15C illustrate a system 400 for, in accordance with an aspect of the present invention, facilitating circumferential adjustments of an implanted annuloplasty prosthesis 402 having purse strings (or flexible chords) 404 and 406. The illustrated example is of the type shown and described with respect to FIG. 13, although those skilled in the art will appreciate that the system 400 may be used to adjust the dimensions of other types of annuloplasty prostheses having purse (or draw) strings. For example, a flexible or rigid bridge may also be employed to connect between the ends of the C-shape prosthesis to form a generally D-shaped prosthesis, such as shown and described with respect to FIG. 14.

The system 400 includes a retaining clip 410 through which ends 412 and 414 of the respective chords 404 and 406 are threaded. FIG. 15B shows an enlarged view of the retaining clip 406. The retaining clip 410 has a pair of holes 420 and 422 that are dimensioned to tightly grip the respective chords 404 and 406 so as to inhibit axial movement of the chords through the holes relative to the clip. The clip 410 also may have a radially extending flange 424.

In order to facilitate movement of the chords 404 and 406 through the respective holes 420 and 422, the ends 412 and 414 of the chords may be gripped, such as with forceps 426, and the clip 410 urged along the length of the chords in a selected direction. The clip may be moved by an instrument (e.g., another pair of forceps (not shown)) or by the surgeon's hands.

In accordance with an aspect of the present invention, an elongated cylindrical member 428 may be employed to urge the clip 410 relative to the chords 404 and 406. The cylindrical member 428 may be formed of a biocompatible metal or plastic material. The ends 412 and 414 of the chords are threaded through the cylindrical member 428. For example, the cylindrical member 428 may include a pair of elongated apertures that substantially align with the holes 420 and 422 of the clip 410. The cylindrical member 428 has a distal end 430 for engaging the clip 410 and urging it along the length of the chords 404 and 406 toward the prosthesis 402. The cylindrical member 428 thus may urge the clip 410 into engagement with the prosthesis 402, as shown in FIG. 15C. The flange 424 inhibits penetration of the clip 410 into the prosthesis 402. As additional lengths of the chords 404 and 406 are pulled from the interior lumen of the prosthesis 402 and through the clip 410, the circumference (or annular length) of the prosthesis may be reduced based on the remaining length of the chords disposed within the prosthesis. For example, the distance between opposed ends of the prosthesis, indicated at D1 in FIG. 15A, also may be reduced to D2, shown in FIG. 15C. As the dimensions of the prosthesis 402 are reduced, it also urges a corresponding reduction in the dimensions of the valve annulus to which the prosthesis is attached.

By way of example, after the prosthesis 402 is implanted [but before completely closing the heart 434], the heart valve 436 may be monitored via an echocardiogram (2-D echo) or another imaging modality (not shown) to ensure proper dynamics of the valve. If the valve 436 still exhibits undesirable regurgitation of blood, such as due to malcoaptation of the leaflets, the dimensions of the valve may be adjusted in accordance with an aspect of the present invention. In particular, the ends 412 and 414 of the chords extend from an exposed end 438 of the cylindrical member 428 (protruding from a small opening in the heart 434). A surgeon may pull a length of the chords from the interior lumen of the prosthesis, such as by urging the clip 410 distally (the direction indicated by arrow 440) towards the prosthesis 402 while simultaneously pulling the ends 412 and 414 proximally, indicated by arrow 442. As a result, the length of the chords 404 and 406 within the lumen of the prosthesis 402 is reduced, which, in turn, reduces the annular extent (or circumferential dimension) of the C-shaped prosthesis. Once it is determined (based on imaging) that the regurgitation has ceased, the surgeon may stop pulling the chords 404 and 406 through the clip 410. Advantageously, the retaining clip 410 maintains the relative length of chords 404 and 406 within the prosthesis 402 so that the annulus is supported at a desired size and/or configuration.

Once the valve is operating in a satisfactory manner, the cylindrical member may be removed and the two ends of the chords 412 and 414 may be tied to further inhibit movement of the retaining clip 410. An excess length of chords 404 and 406 may be cut and the heart 434 may be closed in a conventional manner upon completing the procedure. It is to be appreciated that the dimension and/or configuration of each side portion of the prosthesis 402 may be adjusted independently by shortening the length of a chord 404 or 406 in a corresponding side portion. Moreover, it may be desirable to employ a cylindrical member 428 covered with a biocompatible animal tissue material (e.g., animal pericardium), such as a NO-REACT® tissue product that has undergone an anti-calcification treatment to render the member totally biocompatible. When covered with such a biocompatible material, the cylindrical member 428 may be left in the heart. As a result, if re-operation is necessary to adjust the dimensions of the prosthesis, the procedure may be simplified.

What has been described above are examples of the present invention. It is, of course, not possible to describe every conceivable combination of components or methodologies for purposes of describing the present invention, but one of ordinary skill in the art will recognize that many further combinations and permutations of the present invention are possible. For example, while the figures and description are directed to a mitral valve, it is to be understood and appreciated that annuloplasty prosthesis in accordance with the present invention also may be used to support a tricuspid valve. Accordingly, the present invention is intended to embrace all such alterations, modifications and variations that fall within the spirit and scope of the appended claims. Furthermore, to the extent that the term "includes" is used in either the detailed description and the claims, such term is intended to be inclusive in a manner similar to the term "comprising."

What is claimed is:

1. An annuloplasty prosthesis for supporting an annulus of a heart valve, comprising:
   a tubular sheath of a biocompatible animal tissue material having a lumen within the sheath;
   a length of a substrate disposed within the lumen to facilitate implantation of the sheath at the annulus of the heart valve; and
   an implantation flange extending from a sidewall portion of the tubular sheath.

2. A prosthesis as set forth in claim 1, wherein the implantation flange is an integral part of the tubular sheath.

3. A prosthesis as set forth in claim 1, wherein the substrate is a generally C-shaped ring of a substantially resilient material so as to provide a generally C-shaped prosthesis.

4. A prosthesis as set forth in claim 3, wherein the generally C-shaped prosthesis has opposed ends and the prosthesis further includes a bridge of flexible material connected between opposed ends of the C-shaped prosthesis so as to form a generally D-shaped prosthesis.

5. A prosthesis as set forth in claim 4, wherein the length of flexible material is part of the sheath of animal tissue.

6. A prosthesis as set forth in claim 4, wherein the length of flexible material is formed of animal pericardium.

7. A prosthesis as set forth in claim 4, wherein the bridge of flexible material has a lumen extending through the bridge of flexible material, the lumen connecting the ends of the C-shaped prosthesis portion.

8. A prosthesis as set forth in claim 3, further including a length of generally rigid material extending between opposed ends of the C-shaped prosthesis portion so as to form a generally D-shaped prosthesis.

9. An annuloplasty prosthesis for supporting an annulus of a heart valve, comprising:
   a tubular sheath of a biocompatible animal tissue material having a lumen within the sheath; and
   a length of a substrate of substantially soft core of material having ends spaced apart from each other disposed within the lumen to facilitate implantation of the sheath at the annulus of the heart valve.

10. A prosthesis as set forth in claim 9, further including a bridge of flexible material connecting opposite ends of the tubular sheath, thereby forming a D-shaped prosthesis.

11. A prosthesis as set forth in claim 10, wherein the bridge of flexible material is part of the sheath of animal tissue.

12. A prosthesis as set forth in claim 10, wherein the bridge of flexible material has a lumen extending substantially between the opposite ends of the substrate, an elongated rod being disposed in the lumen of the bridge of flexible material.

13. A prosthesis as set forth in claim 10, further including a flexible cord extending longitudinally through a lumen extending through the tubular sheath adjacent the substrate, two ends of the cord extending through the ends of the tubular sheath, the prosthesis having a circumferential dimension that varies according to the length of the flexible cord disposed within the tubular sheath.

14. An annuloplasty prosthesis for supporting an annulus of a heart valve, comprising:
   a tubular sheath of a biocompatible animal tissue material having a lumen within the sheath;
   a length of a substrate disposed within the lumen to facilitate implantation of the sheath at the annulus of the heart valve; and
   two lengths of a flexible cord, each length of cord having an end portion fixed relative to an opposite end of the tubular sheath, each length of cord extending from the respective fixed end through at least part of a lumen within the tubular sheath and extending through the tubular sheath at a location intermediate the opposite ends of the tubular sheath to terminate in terminating ends located external to the tubular sheath, the prosthesis having a dimension that varies according to the length of each cord disposed within the tubular sheath.

15. A prosthesis as set forth in claim 14, further including a retaining clip having at least one aperture through which the terminating ends of the cords are threaded, wherein the retaining clip inhibits axial movement of each of the cords through the retaining clip to facilitate maintaining a desired length of each cord disposed within the tubular sheath.

16. A prosthesis as set forth in claim 15, further including an implantation flange extending from a sidewall portion of the tubular sheath.

17. A prosthesis as set forth in claim 15, wherein the substrate is a generally C-shaped ring of a substantially resilient material so as to provide a generally C-shaped prosthesis.

18. A prosthesis as set forth in claim 17, wherein the generally C-shaped prosthesis has opposed ends and the prosthesis further includes a bridge of flexible material connected between opposed ends of the C-shaped prosthesis so as to form a generally D-shaped prosthesis.

19. A prosthesis as set forth in claim 18 wherein the bridge of flexible material is animal pericardium.

20. A prosthesis as set forth in claim 14, further including wherein each flexible cord is a suture material.

21. A prosthesis as set forth in claim 9, wherein the substrate further includes a radio-opaque material.

22. A prosthesis as set forth in claim 21, wherein the animal tissue material is animal pericardium.

23. An annuloplasty prosthesis for supporting an annulus of a heart valve, comprising:
   a generally C-shaped substrate of a substantially resilient material having spaced apart ends;
   a sheath of a biocompatible animal tissue material covering the C-shaped substrate to form a generally C-shaped prosthesis; and
   an implantation flange extending outwardly from a sidewall portion of the sheath.

24. A prosthesis as set forth in claim 23, further including a bridge of a flexible material connecting opposed ends of a C-shaped portion of the prosthesis, thereby forming a generally D-shaped prosthesis.

25. A prosthesis as set forth in claim 24, wherein the bridge of flexible material is formed of animal pericardium.

26. A prosthesis as set forth in claim 23, wherein the implantation flange is formed of animal tissue material extending from an outer periphery of the prosthesis.

27. A prosthesis as set forth in claim 26, further including a bridge of a flexible material connected between opposed ends of a C-shaped portion of the prosthesis, the bridge of flexible material being formed from part of the sheath.

28. A prosthesis as set forth in claim 27, wherein the implantation flange is an integral part of the sheath.

29. A prosthesis as set forth in claim 27, further including a generally rigid material disposed within a lumen of the bridge of flexible material.

30. A prosthesis as set forth in claim 23, further including two lengths of a flexible cord, each length of cord having an end portion fixed relative to an opposed end of the C-shaped prosthesis portion, each length of cord extending from the respective fixed end through at least part of a lumen within the sheath and extending through an exterior portion of the sheath at a location intermediate the opposed ends of a C-shaped portion of the prosthesis to terminate in terminating ends located external to the sheath, the prosthesis having a dimension that varies according to the length of each cord disposed within the sheath.

31. A prosthesis as set forth in claim 30, further including a retaining clip having at least one aperture through which the terminating ends of the cords are threaded, wherein the retaining clip inhibits axial movement of each of the cords through the retaining clip to facilitate maintaining a desired length of each cord disposed within the sheath.

32. A prosthesis as set forth in claim 1, wherein the substrate is a generally C-shaped ring of a substantially resilient material so as to form a generally C-shaped prosthesis portion, the bridge connecting ends of the C-shaped prosthesis portion.

33. A prosthesis as set forth in claim 1, wherein the substrate includes a soft flexible core.

34. A prosthesis as set forth in claim 1, wherein the sheath is animal pericardium.

35. A prosthesis as set forth in claim 34, wherein the bridge is an integral part of the sheath.

36. An annuloplasty prosthesis for supporting an annulus of a heart valve, comprising:
   a length of a substrate having spaced apart ends;
   a sheath of a biocompatible animal tissue material completely covering the substrate;
   a bridge of flexible material extending between spaced apart ends of the sheath so as to define a generally D-shaped prosthesis; and two lengths of a flexible cord, each length of cord having an end portion fixed relative to an opposed end of a C-shaped portion of the D-shaped prosthesis, each length of cord extending from the respective fixed end through at least part of a lumen within the sheath and extending through an exterior portion of the sheath at a location intermediate the opposed ends of a C-shaped prosthesis portion to terminate in terminating ends located external to the sheath, the prosthesis having a circumferential dimension that varies according to the length of each cord disposed within the sheath.

37. A prosthesis as set forth in claim 36, further including a retaining clip having at least one aperture through which the terminating ends of the cords are threaded, wherein the retaining clip inhibits axial movement of each of the cords through the retaining clip to facilitate maintaining a desired length of each cord disposed within the sheath.

38. An annuloplasty prosthesis for supporting an annulus of a heart valve, comprising:
   a tubular sheath of a biocompatible animal tissue material having a lumen within the sheath;
   a length of a generally C-shaped substrate disposed within the lumen to facilitate implantation of the sheath at the annulus of the heart valve so as to form a generally C-shaped prosthesis portion;
   a bridge of a flexible material connected between ends of the sheath and having a lumen extending through the bridge of flexible material so as to provide a generally D-shaped prosthesis; and
   a stiffening element disposed within the lumen of the bridge of flexible material and extending between the ends of the C-shaped prosthesis portion.

* * * * *